US012678206B2

(12) United States Patent
Mullis et al.

(10) Patent No.: US 12,678,206 B2
(45) Date of Patent: Jul. 14, 2026

(54) SCREW, SYSTEM COMPRISING A SCREW AND A PLATE, AND METHOD FOR PRODUCING A SCREW

(71) Applicant: MEDARTIS HOLDING AG, Basel (CH)

(72) Inventors: Andreas Mullis, Hemmiken (CH); Dirk Thiel, Staufen (DE); Patrick Mark Sesiani, Schwörstadt (DE); Stefan Olivier Würger, Lausen (CH); Jürgen Schonhardt, Rheinfelden (DE); Hermann Zeuner, Freiburg (DE)

(73) Assignee: MEDARTIS HOLDING AG, Basel (CH)

( * ) Notice: Subject to any disclaimer, the term of this patent is extended or adjusted under 35 U.S.C. 154(b) by 803 days.

(21) Appl. No.: 17/910,190

(22) PCT Filed: Mar. 10, 2021

(86) PCT No.: PCT/EP2021/056072
§ 371 (c)(1),
(2) Date: Sep. 8, 2022

(87) PCT Pub. No.: WO2021/180799
PCT Pub. Date: Sep. 16, 2021

(65) Prior Publication Data
US 2023/0103083 A1      Mar. 30, 2023

(30) Foreign Application Priority Data
Mar. 11, 2020      (EP) ..................................... 20162460

(51) Int. Cl.
*A61B 17/80*      (2006.01)
*A61B 17/86*      (2006.01)

(52) U.S. Cl.
CPC ...... *A61B 17/8057* (2013.01); *A61B 17/8605* (2013.01); *A61B 17/866* (2013.01)

(58) Field of Classification Search
CPC ............ A61B 17/8057; A61B 17/8605; A61B 17/866
See application file for complete search history.

(56) References Cited

U.S. PATENT DOCUMENTS 6,306,140 B1 *  10/2001  Siddiqui .............. A61B 17/863
                                                                     606/315
8,403,972 B2     3/2013  Hasenböhler et al.
(Continued)

FOREIGN PATENT DOCUMENTS

DE      10 2010 038 949 A1      2/2012
JP           2008-296311 A      12/2008
(Continued)

OTHER PUBLICATIONS

Japanese Office Action Corresponding to 2022-554647 mailed Aug. 20, 2024.
(Continued)

*Primary Examiner* — Kevin T Truong
*Assistant Examiner* — Diana Jones
(74) *Attorney, Agent, or Firm* — Secant IP, P.L.L.C.

(57)      ABSTRACT

The invention relates to a screw (1), preferably a bone screw, comprising a shaft (2) with a tip (3), a head (4) and a thread (5). The shaft further comprises a longitudinal axis (A). An array of radial cross-sectional surfaces (Q) of the head (4) extend through the longitudinal axis (A) of the screw (1), the location of each radial cross-sectional surface (Q) being defined by an azimuth angle (6) in a plane (E) perpendicular to the longitudinal axis (A). Each radial cross-sectional area (Q) has an area defined by the longitudinal axis (A) and the outer surface of the screw (8). The thread (5) extends into the
(Continued)

Figure 4:
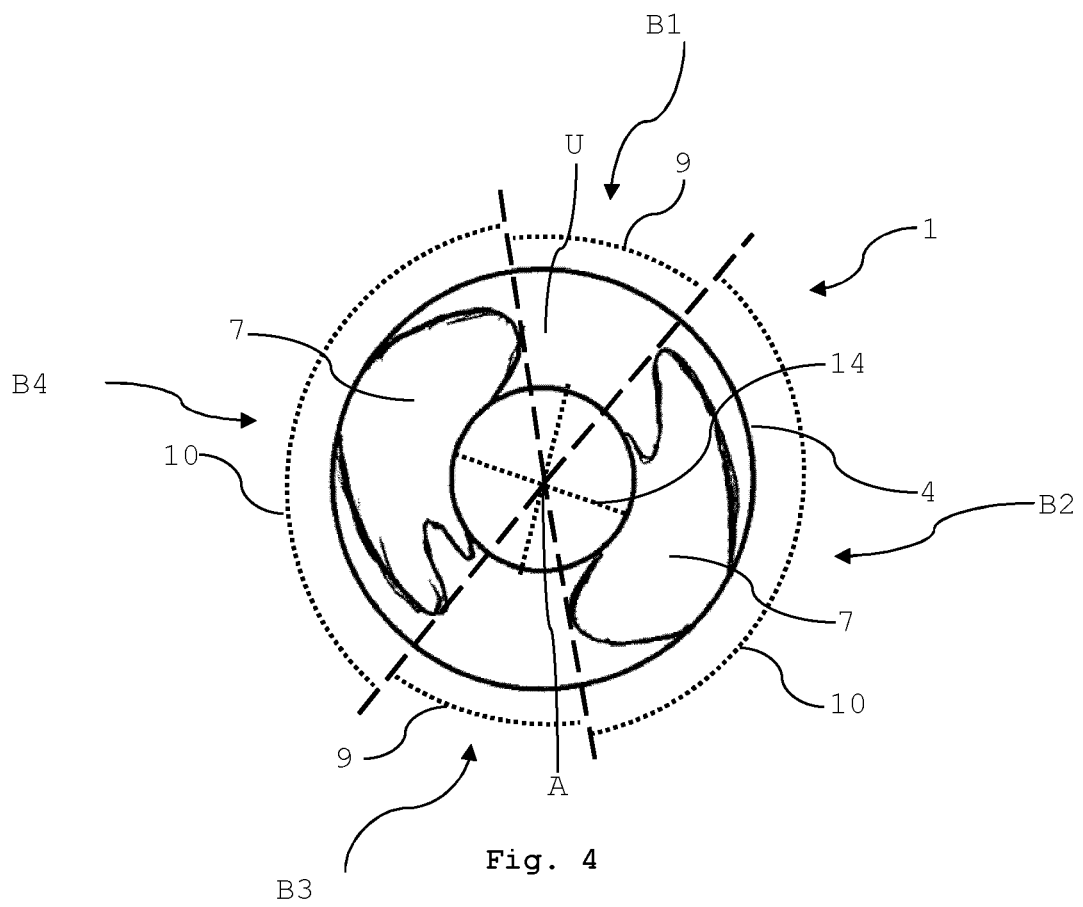

head (4) in such a way that the surface areas of the radial cross-sectional surfaces (Q') in a first azimuth angle range (9) are constant and the surface areas of the radial cross-sectional surfaces (Q") in a second azimuth angle range (10), which is different from the first, have a different, preferably smaller, value than the surface areas in the first azimuth angle range (9). The first azimuth angle range (9) is at most 350°, preferably at most 345°.

13 Claims, 4 Drawing Sheets

(56) References Cited

U.S. PATENT DOCUMENTS

| | | | | |
|---|---|---|---|---|
| 2014/0277180 A1* | 9/2014 | Paolino | .............. | A61B 17/8605 |
| | | | | 606/291 |
| 2015/0051651 A1 | 2/2015 | Terrill et al. | | |
| 2016/0015439 A1* | 1/2016 | Wolter | .................. | A61L 31/022 |
| | | | | 606/305 |
| 2018/0235681 A1* | 8/2018 | Chambers | ............ | A61B 17/861 |

FOREIGN PATENT DOCUMENTS

| | | | |
|---|---|---|---|
| JP | 2012-161854 | A | 8/2012 |
| KR | 101 772 535 | B1 | 8/2017 |
| WO | 00/66012 | A1 | 11/2000 |
| WO | 2007/048267 | A1 | 5/2007 |

OTHER PUBLICATIONS

Partial European Search Report Corresponding to 20162460.8 mailed Sep. 8, 2020.
Partial International Search Report Corresponding to PCT/EP2021/056072 mailed Jun. 4, 2021.
International Search Report Corresponding to PCT/EP2021/056072 mailed Jul. 27, 2021.
Written Opinion Corresponding to PCT/EP2021/056072 mailed Jul. 27, 2021.
European Search Report Corresponding to 20162460.8 mailed Nov. 9, 2020.

* cited by examiner

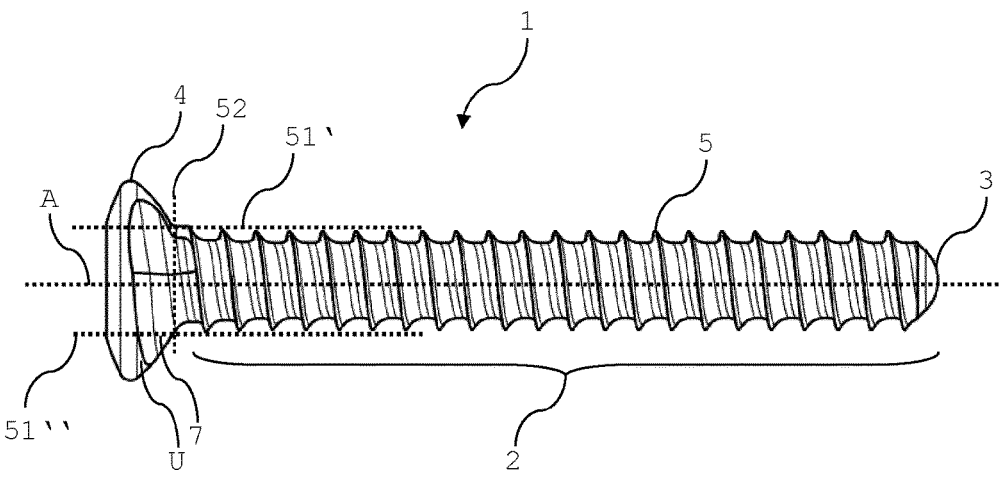
Fig. 1
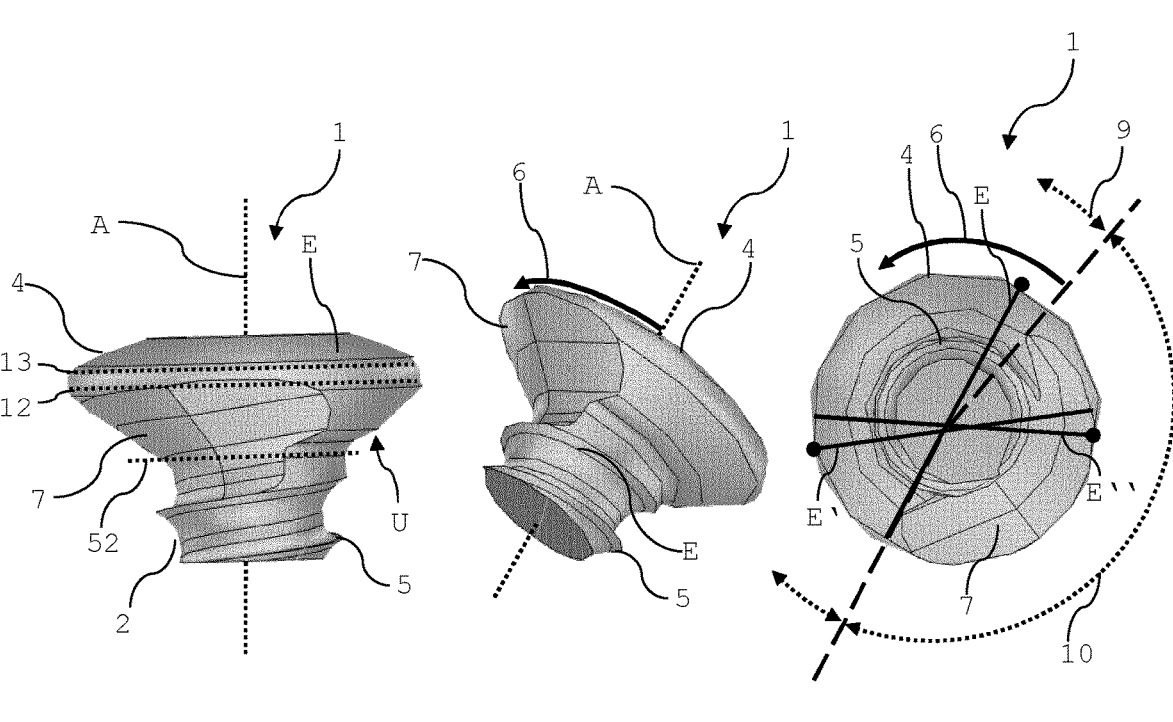
Fig. 2a                    Fig. 2b                    Fig. 2c

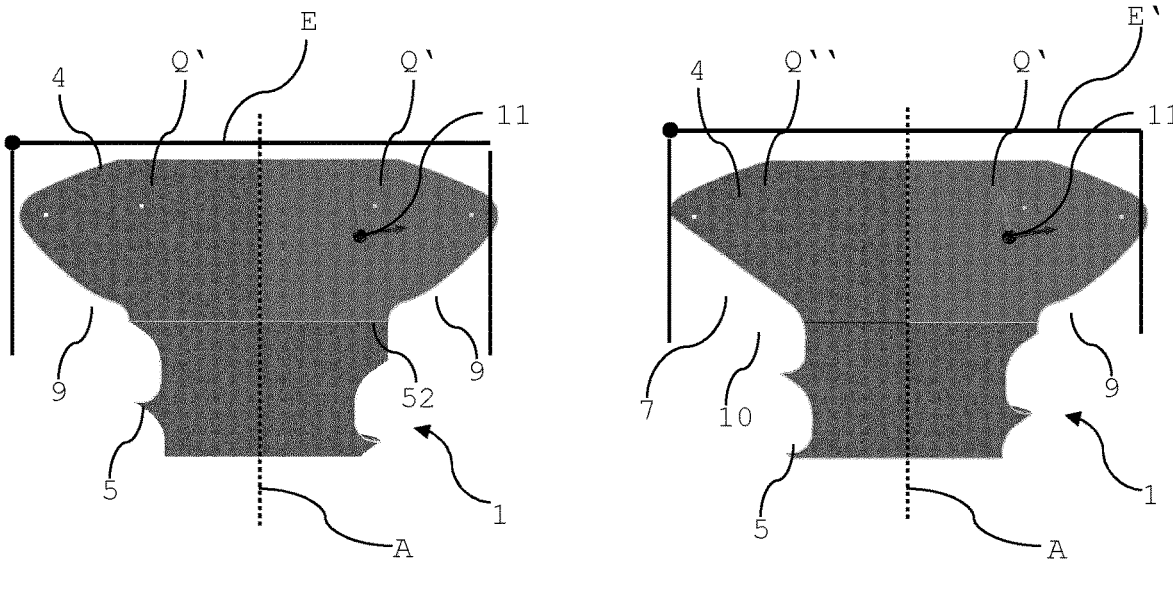
Fig. 3a                                        Fig. 3b
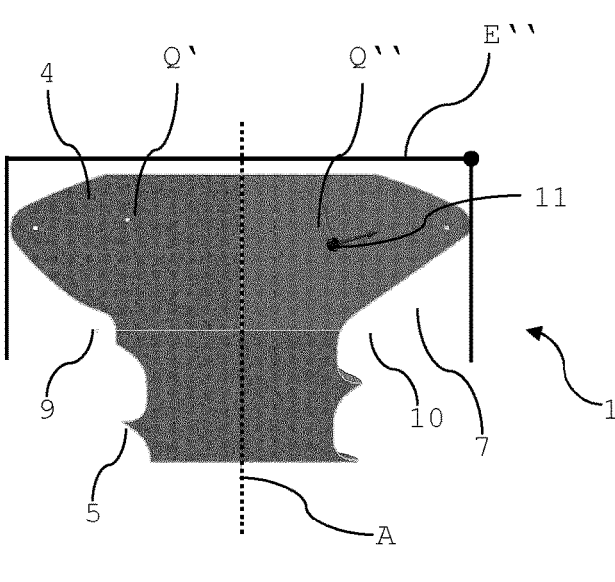
Fig. 3c

SCREW, SYSTEM COMPRISING A SCREW AND A PLATE, AND METHOD FOR PRODUCING A SCREW

The invention relates to a screw, a system comprising a screw and a plate, and a method for producing a screw according to the preamble of the independent claims.

It is known to use screws to connect implants to bone. For example, certain bone fractures are treated by connecting the fractured bones by means of a bone plate and fixing them in place with screws.

Known screws have various disadvantages. For example, conventional screws can often not be used if the bone to be connected has a thin cortical layer, as the screw can then not sufficiently engage with the bone. Similarly, conventional screws can be aesthetically disadvantageous when used under thin tissue layers because thick plates are required for secure anchorage in the bone.

It is therefore the object of the present invention to overcome the disadvantages of the prior art and, in particular, to provide a screw which offers greater flexibility of use. For example, the screw should also be suitable for use with thin plates and/or for connection to thin bones, thus enabling a wider range of applications.

These and other advantages are achieved by a screw, a system comprising a screw and a plate, and a method of manufacturing a screw according to the characterizing portion of the independent claims.

The screw according to the invention is preferably a bone screw and comprises a shaft with a tip, a head and a continuous thread, as well as a longitudinal axis of the shaft. Further, the screw comprises a set of radial cross-sectional areas of the head bounded by the longitudinal axis of the shaft. The location of each radial cross-sectional surface is defined by an azimuth angle in a plane perpendicular to the longitudinal axis. Each radial cross-sectional area has an area defined by the longitudinal axis and the outer surface of the screw. According to the invention, the thread extends into the head in such a way that the areas of the radial cross-sectional surfaces are constant in a first azimuth angle range. The surface areas of the radial cross-sectional areas in a second azimuth angle range have a different, preferably smaller, value than the surface areas of the first azimuth angle range. The first azimuth angle range is different from the second azimuth angle range. The first azimuth angle range is at most 350°, preferably at most 345°. Preferably, the thread extends substantially from the tip of the screw at least to the head, particularly preferably into the head.

However, it is also conceivable that the thread does not start at the tip of the screw and/or is interrupted and extends substantially to the head, particularly preferably into the head. It is conceivable that a thread only extends into the head over in an azimuth angle range, preferably in the second azimuth angle range. In this case, there is a complementary azimuth angle range in which a screw according to the invention does not comprise a thread at and/or in the head. However, it is also conceivable that the thread extends over an entire circumferential region of the screw into the head.

As a result, the thread extends closer to the screw head than with conventional screws and, in particular, into the head. Therefore, the screw can also engage the bone when using thin plates and/or when treating bones with thin cortical layers. A radial cross-section of the head shall be understood as the part of the total cross-sectional area of the head that lies on one side of the longitudinal axis and is bounded by the longitudinal axis. A cross-section of the head therefore has, by definition, two radial cross-sections.

A continuous thread is designed in such a way that the thread has a starting point and an end point and no thread-free sections are arranged in between. In particular, a continuous thread has a constant thread pitch between the start and end points. A continuous thread can be multi-threaded. Particularly preferably, the starting point is located substantially at the screw tip and/or the end point is located substantially in a region of the screw head.

Particularly preferably, the shape of the thread is substantially the same in all thread parts, especially over the entire length along the screw axis over which the thread extends. In particular, the thread pitch and the inner and outer thread diameters can be constant over the entire length. In particular, the envelope of the outer diameter of the screw may extend substantially parallel to the longitudinal axis of the screw.

It is additionally or alternatively conceivable that a thread section, preferably a finishing section of the thread which extends into the screw head, has a different thread diameter. It is understandable for the person skilled in the art that such a finishing section with a deviating thread diameter is not in contradiction to a thread described above with essentially the same thread form over the entire thread length.

Alternatively, it is also conceivable that the thread has different thread diameters along the longitudinal axis of the screw. In particular, the thread may have a preform area and/or an intermediate area and/or an anchoring area as described in WO 2007/048267, which is incorporated by reference. Thus, the screw may also be self-tapping and/or self-drilling.

The screw therefore preferably has exactly one continuous thread. This can extend in particular from the tip into the head. The thread section that extends into the head can in particular also be designed only as a stub.

The screw according to the invention is particularly advantageous when using and fixing bone plates with a thickness of 0.1 to 1 mm. Such thin plates are particularly advantageous in the treatment of bones with thin soft tissue coverage. However, also in bones with thin cortical bone, in particular in a range of 0.1 to 2 mm and/or poor spongiosa quality and/or with monocortical anchorage, the screw according to the invention offers a more secure hold compared to the prior art.

The area contents comprise only the area of the radial cross-sectional surface on one side of the longitudinal axis. Each cross-sectional area therefore comprises two radial cross-sectional areas, each with a surface area whose position is defined by an azimuth angle that differs by 180°.

In particular, the azimuth angle, which defines the position of the respective surface areas, can be understood as a relative indication to an arbitrary zero point. Preferably, the end of the thread is used as the zero point. In this case, the surface area with an azimuth angle of 0° is by definition assigned to the first azimuth angle range, while the directly adjacent surface area (with an azimuth angle greater than 359°) is by definition assigned to the second azimuth angle range. This example serves only for a better understanding of the description of the invention. It is analogously possible to choose any zero point for the definition of the position of the area contents.

For the calculation of the surface areas, non-thread related contours should be excluded. For example, a drive (such as Torx, Phillips, slot) can be arranged in the screw head, which would change the surface areas of the radial cross-sectional areas non-uniformly due to lack of rotational symmetry. In this case, the drive can be filled in mentally, so that the drive has no significance for the calculation of the surface areas.

Preferably, the area in a direction of the longitudinal axis in the direction of the screw head can also be included only up to the equator, i.e. up to the widest point of the screw head in a plane perpendicular to the longitudinal axis.

The head of the screw can be understood in particular as a region of the screw along the longitudinal axis which extends in a plane perpendicular to the longitudinal axis in the radial direction at least partially over the thread, in particular an outer radius of the thread. Accordingly, the surface areas of the radial cross sections can also be calculated in such a way that the area of the screw which, according to the above definition, does not belong to the head, is not included.

The screw may comprise a material from the group of titanium, titanium alloys and implant steel. However, other biocompatible materials are also conceivable. Preferably, the screw consists of one of the materials mentioned.

The screw can preferably have a thread with a thread pitch of 0.4 to 0.6 mm with a thread diameter of 0.9 or 1.2 mm.

Alternatively, the screw can have a thread pitch of 0.5 to 0.75 mm with a thread diameter of 1.5 or 1.8 mm.

However, other thread diameters and thread pitches are conceivable, in particular thread diameters from 0.5 to 2.5 mm and thread pitches from 0.1 to 1.5 mm.

Preferably, the screw has a drive selected from a group comprising slot, cross, polygonal, Torx and Phillips.

For two-, three- or multi-threaded screws, the first and second azimuth angle regions may be divided into at least two, and in particular two or three or more, sections distributed at equal azimuth angle intervals.

This means that the complete circumferential angle range is divided into the corresponding multiple number of sections. The first and second azimuth angle ranges alternate in this case. For example, if the first and second azimuth angles are divided into two sections, the two sections of the first azimuth angle range are each bounded by the sections of the second azimuth angle range.

In particular, the azimuth angle distance can be measured from the center of the respective sections and in this case is preferably 180° or 120°.

The first azimuth angle range can also be at most 330°, preferably at most 305°.

The specified azimuth angle range is to be understood as the sum of the individual sections of the respective azimuth angle ranges.

The thread of the screw can be multi-threaded, preferably two or three threads.

The first azimuth angle range can also be at most 340°, 320°, 315°, or 300°, especially for multi-threaded threads. For multi-threaded threads with n threads, the second azimuth angle range is particularly preferably at least n×15°. In this case, the first azimuth angle range is therefore at most the difference between 360° and n×15°.

If the thread is multi-threaded, the azimuth angle range may be divided into as many sections as the number of threads.

Preferably, in the second azimuth angle range, the head has at least one indentation formed by the continuation of the thread.

In particular, the indentation may be created by a whirling knife used to create the thread. The indentation can allow the screw to be screwed deeper into the bone, particularly into the hard cortical bone immediately below the plate, before the screw head rests on a bone plate, for example. This makes the treatment more stable because threaded portions just below the head can still be anchored in the bone, and damage to the bone can be reduced. The head may have a number of such indentations equal to the number of sections.

Preferably, each portion of the second azimuth angle range has at least one indentation formed by the continuation of the thread.

In particular, the indentation can be shaped like a stump and can also have an at least partially elliptical area. Particularly preferably, the indentation has different widths in the circumferential direction, with the thickness initially increasing in the direction of the thread run and decreasing again in an end section. In this case, the maximum width of the indentation can be located in an area where the thread ends in the shaft. The at least one indentation formed by the continuation of the thread may be located on an underside of the head in the region of the thread finish.

The underside of the head can be understood in particular as the area of the surface of the head whose normal direction points at least partially in the direction of the tip of the screw shaft, in particular with respect to a plane perpendicular to the longitudinal axis. The underside of the head comprises the area of the surface of the head which is located on the side of the tip of the shaft, as seen from the equator of the head.

The radial cross-sectional surfaces have a geometric center. A geometric center is to be understood according to the common definition. The geometric center of the radial cross-sectional surfaces in the first azimuth angle range may each have the same distance to the longitudinal axis. Preferably, the geometric center of the radial cross-sectional surfaces in the first azimuth angle range has an identical position relative to the longitudinal axis.

Particularly preferably, the radial cross-sectional areas in the first azimuth angle range also have an identical shape. Particularly preferably, the radial cross-sectional areas within the second azimuth angle range have at least partially different shapes. However, it is conceivable that the radial cross-sectional surfaces in the second azimuth angle range also have an identical shape. Even in this case, however, the areas of the radial cross sections in the second azimuth angle range would be smaller than in the first azimuth angle range.

If the second azimuth angle range is divided into sections, it is particularly preferred that the radial cross-sectional areas in one section have identical shapes to the radial cross-sectional areas in at least one other section, preferably all other sections. In this case, it is possible that the radial cross sections within a section have identical or different shapes.

The screw may be shaped, particularly formed, so that each radial cross-sectional area is connected, particularly path connected or simply connected.

A surface is path connected if any two points on the surface can be connected by a path within the surface.

A surface is simply connected if it is connected and any closed line can be contracted to a point.

In particular, the screw head thereby does not comprise any through holes or holes. In particular, the screw head preferably does not comprise any holes or holes connecting the longitudinal axis to the surface of the screw or head.

The screw, in particular the head of the screw, may have a first normal cross-section in a plane perpendicular to the longitudinal axis in the head region of the screw that is non-circular.

Preferably, the screw, in particular the head of the screw, has a second normal cross-section which is circular and parallel to the first normal cross-section. The first normal cross-section is thereby preferably arranged along the longitudinal axis of the screw between the tip of the screw and the second normal cross-section.

The invention further relates to a system comprising a bone plate and a bone screw. In particular, the system may comprise a bone screw having the features described above. The bone plate includes at least one opening for insertion of the bone screw. The bone screw includes a head, a shaft, and a thread therethrough. Preferably, the bone plate has a thickness that is at most equal to the length of the head of the screw along a longitudinal axis of the screw. In particular, the thickness of the plate may have a value between 0.1 to 1 mm. The bone screw is insertable into the opening of the bone plate such that the head is in mechanical contact with the bone plate, in particular rests on the bone plate, and the thread extends at least partially into the opening.

The invention further relates to a method for producing a screw, in particular a bone screw. Preferably, the method is used to produce a screw as described above. The screw is manufactured according to the method of the invention using a tool, in particular selected from a group comprising whirling knives and thread milling cutters. However, other comparable tools are also conceivable. The method comprises providing a slug material having a substantially cylindrical shape, and cutting a thread along a longitudinal axis of the cylindrical shape with the tool. A head is also formed, in particular turned. The screw is then gripped by means of a contour collet. The contour collet has a contour which is adapted to a contour of the head or parts of the head and which, in the gripped state, is in operative connection with a counter-contour of the head or parts of the head. Optionally, it is also possible to additionally grip at least partially on parts of the shank, the neck or the thread.

This allows the screw to be gripped without damaging the thread, which extends into the screw head.

Preferably, a head is first turned into the slug material, and then the thread is cut.

Preferably, the contour of the contour collet is at least partially designed to be essentially complementary to the mating contour of the head or parts of the head and parts of the neck or thread of the screw. As a result, the contour fits at least partially exactly to the mating contour, which enables a particularly secure holding.

Preferably, the thread is cut by the tool so close to the head that the tool forms an indentation on an underside of the head. In particular, this is done when the head is turned before the thread is cut. However, it is also conceivable that the shape of the head is turned only after the thread has been cut.

Preferably, a tool is used which has a whirling plate, whereby the whirling plate does not enclose an overcutting edge in a cutting direction on the leading surface, i.e. in the direction of the screw head and away from the already cut thread. The whirling plate can therefore penetrate deeper into the screw head without leaving an imprint of the overcutting edge.

Preferably, after cutting the thread with the tool, the head is further machined using a CNC lathe. In particular, a screw drive, for example a Torx drive, can be manufactured.

Preferably, exactly one thread is cut, with the entire thread being produced with the same tool. In this way, a screw can be produced which comprises exactly one thread, whereby the thread can have the same thread pitch and/or constant inner and outer thread diameters over the entire length.

Preferably, the thread is cut from the screw tip to the screw head, particularly preferably in the head.

The invention is explained in detail below with reference to the following figures, showing:

FIG. 1: a screw in a side view.

FIG. 2a-2c: a screw head of a screw in a side view, perspective view, and bottom view.

FIG. 3a-3c: cross-sections of a screw head in planes E, E' and E" of FIG. 2c.

FIG. 4: a bottom view of a head of an alternative embodiment of a screw.

Figure 5:
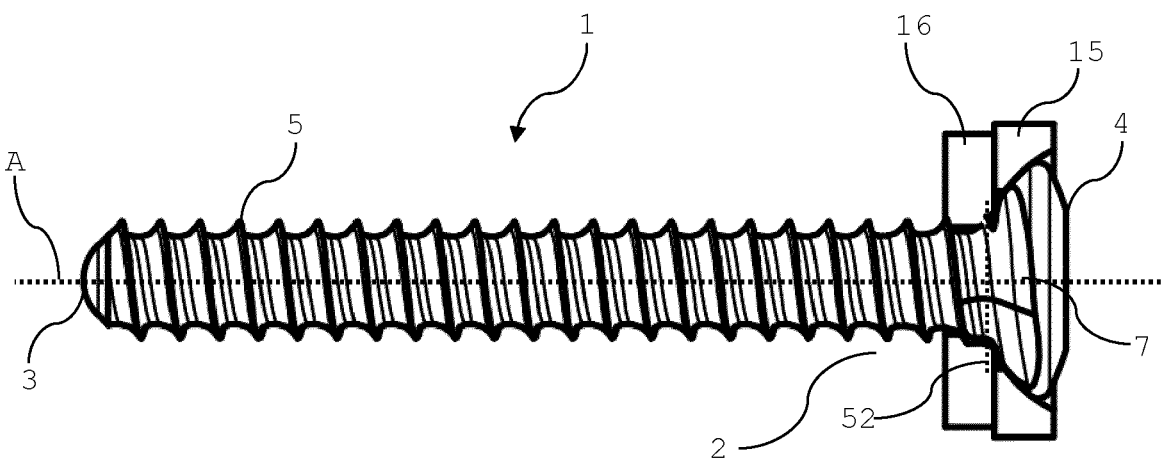

FIG. 5: a bone plate with a screw.

Figure 6:
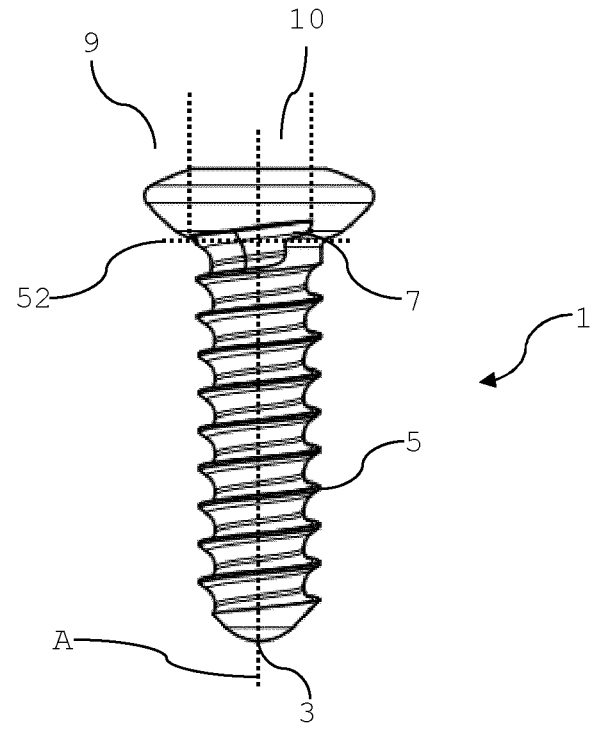

FIG. 6: a side view of an alternative screw.

Figure 7:
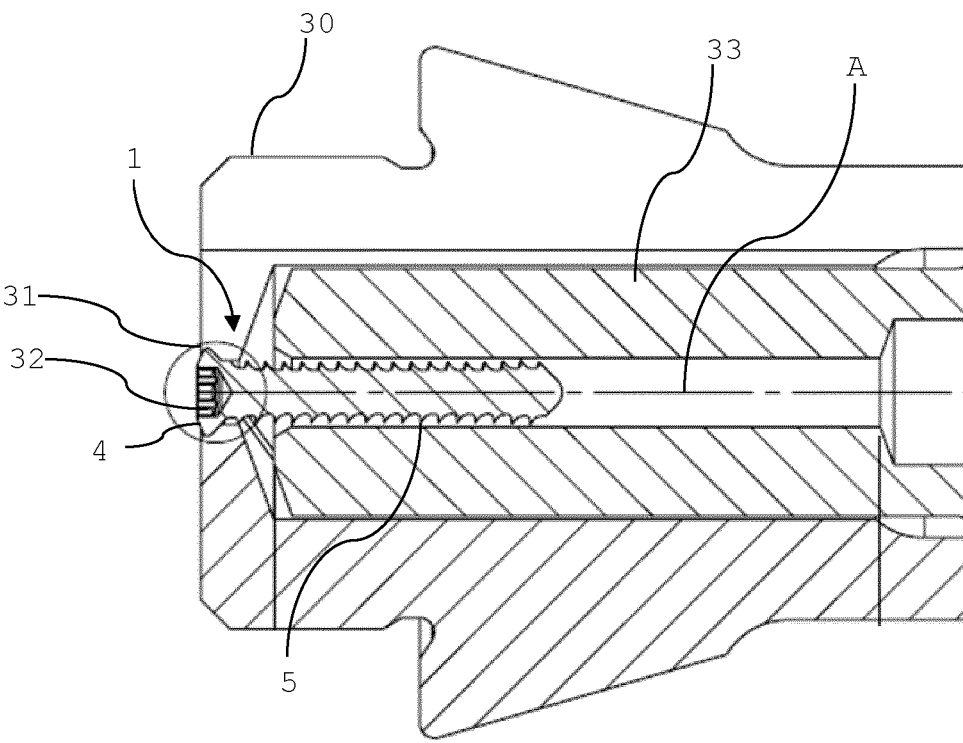

FIG. 7: schematic of a process step for manufacturing a screw.

FIG. 1 shows a screw 1 according to the invention in a side view. The screw 1 comprises a shaft 2 with a tip 3, a thread 5, and a head 4. In the present case, the head 4 is bounded by a plane 52 which is perpendicular to the longitudinal axis A of the screw 1. The plane 52 is positioned along the longitudinal axis A in such a way that the shaft 2 of the screw 1 in the distal direction of the tip 3 (to the right of the plane 52 in FIG. 1) in cross-section perpendicular to the longitudinal axis does not project anywhere beyond the radius of the external thread 51',51". A section in the other proximal direction (to the left of plane 52 in the illustration of FIG. 1), on the other hand, projects beyond the radius of the external thread 51',51" and defines the head 4 of the screw. The thread 5 extends beyond the plane 52 into the head and forms an indentation 7 on the lower side U of the head 4.

FIG. 2a shows the head 4 of the screw 1 according to the invention in a side view. For better understanding, a part of the shaft 2 with the thread 5 is also shown. The plane 52 separates the head 4 from the shaft 2. The thread 5 extends beyond the plane 52 into the head and forms an indentation on the underside of the head. The screw head 4 therefore comprises a first normal cross-section 12 and a second normal cross-section 13. The first normal cross-section 12 intersects the indentation 7 and is therefore non-circular. The second normal cross-section 13 is further away from the screw tip 3 along the longitudinal axis than the first normal cross-section 12. It therefore follows that the first normal cross-section 12 is arranged along the longitudinal axis A between the second normal cross-section 13 and the tip 3. Since the second normal cross-section 13 lies above the indentation 7, the second normal cross-section has a circular shape. A plane E, which is coplanar with the longitudinal axis A, is adjacent to the indentation 7.

FIG. 2b shows the screw head 4 from FIG. 2a in a perspective view. An azimuth angle 6 is drawn in a counterclockwise direction around the longitudinal axis A, with the plane E serving as the zero point for the following figures. As explained above, any other zero point could be selected. It would also be possible to measure the azimuth angle 6 in a clockwise direction. FIG. 2c shows the screw head 4 from FIGS. 2a and 2b in a bottom view. The longitudinal axis A, not shown here, runs perpendicular to the image plane, so that the azimuth angle 6 lies correspondingly in the image plane. A first azimuth angle region 9 has no indentation 7 and extends over an azimuth angle of 195°. The indentation 7 accordingly extends over an azimuth angle of 165° and defines a second azimuth angle range 10. The second azimuth angle range 10 therefore has a value of 165°. Due to the indentation 7, the cross-sections of the screw head 4 in planes through the longitudinal axis, which lie at least partially in the second azimuth angle range 10, are not mirror-symmetrical with respect to the longitudinal axis A. The radial cross-sections bounded by the longitudinal axis A on one side and by the outer surface of the head 4 on the other side have a smaller area in the second azimuth angle region 10 than in the first azimuth angle region 9. This feature is described below by means of cross-section figures in the planes E, E' and E" shown here. As mentioned above, plane E is at an azimuth angle 6 of 0°, plane E' is at an azimuth angle 6 of 135° and plane E" is at an azimuth angle 6 of 300°. All planes are marked here on one side with a dot, which should facilitate the understanding of the plane orientation in the following figures.

FIG. 3a shows a cross-sectional view of the screw head of FIGS. 2a-2c in the plane E. The head 4 is bounded by the plane 52, so that only the area within the boundary of the head 4 and the plane 52 is included for the following discussion of surface areas. Two radial cross sections Q' are each bounded by the outline of the head 4, the longitudinal axis A and the plane 52 and have surface areas Q'. The plane E does not intersect the indentation 7 (not shown here). Therefore, both surface areas Q' are identical and are located in the first azimuth angle area 9. The cross section is mirror symmetrical with respect to the longitudinal axis A. Therefore, the two radial cross sections Q' have the same shape. Finally, the radial cross-sectional area Q' comprises a geometric center 11, which has a distance and a position with respect to the longitudinal axis A. Both position and distance of the geometric center 11 are the same for all surface areas Q' located in the first azimuth angle range 9. The screw head can contain a drive, for example a Torx drive (not shown). This has not been included in the present calculation of the surface areas. Instead, the drive was filled in mentally and its area counted as part of the head 4. It is also evident from FIG. 3a, as well as from the following FIGS. 3b and 3c, that the radial cross-sections Q',Q" are path-contiguous and simply contiguous. This means that all points within the surface can be connected by a path belonging to the surface. In addition, each closed path within the surface can be contracted to one point. This might not be possible with a screw head that contained a hole.

FIG. 3b shows a cross-sectional view of the screw head 4 of FIGS. 2a-2c in the plane E'. Two radial cross sections Q',Q" are each bounded by the outline of the head 4, the longitudinal axis A and the plane 51 and have surface areas. The radial cross sections Q',Q" differ in shape and surface area. The radial cross section Q" is located in the second azimuth angle area 10 and is therefore located in a head area that has an indentation 7. The radial cross section Q" therefore has a smaller surface area than the radial cross section Q'. The radial cross section Q', on the other hand, has the same surface area as well as the same shape as the two radial cross sections Q' from FIG. 3a, since they are located in the first azimuth angle area 9. Likewise, the geometric center 11 of the radial cross section Q' is arranged at the same distance and in the same position relative to the longitudinal axis A as shown in FIG. 3a.

FIG. 3c shows a cross-sectional view of the screw head 4 of FIGS. 2a-2c in the plane E". The representation corresponds essentially to that of FIG. 3b, but the radial cross sections Q' and Q" are oriented in reverse. In the present figure, the geometric center 11 of the radial cross section Q" is drawn. Said geometric center is variable in the second azimuth angle range 10, i.e. it can have a different position and a different distance to the longitudinal axis A depending on the azimuth angle. FIG. 4 shows a head 4 of an alternative embodiment of a screw 1 in a bottom view. The screw head 4 has two indentations 7 on its bottom side U. Such a screw head is particularly suitable for use with multi-threaded, in particular double-threaded, screws. The head areas that have an indentation 7 are located in the second azimuth angle area 10. The first azimuth angle area 9 does not have any indentations 7 and is therefore mirror-symmetrical relative to the longitudinal axis A, which is perpendicular to the image plane. The first azimuth angle region 9 and the second azimuth angle region 10 are each divided into two sections B1,B2,B3,B4, which are bounded by the respective other azimuth angle region 9,10 and are arranged at equal azimuth angle intervals. The bisecting line 14 of the boundaries of the sections is preferably used as the reference point for determining the angular separation. Therefore, the angular distance between the sections is 90°. The first azimuth angle range 9 has a total value of 90°, which is distributed over two sections of 45° each. Furthermore, when the screw head 4 shown is used with a screw with a double thread, the head 4 has the same number of sections as the thread has threads. Furthermore, each section of the second azimuth angle area 10 then has exactly one indentation 7.

FIG. 5 shows a screw 1 in the screwed-in state with a bone plate 15 in a thin cortical layer 16. The screw 1 corresponds essentially to the screw 1 shown in FIG. 1. Also shown is the plane 52 separating the head 4 from the shaft 2. Due to the indentation 7 and the thread 5 extending into the head 4, the thread 5 engages over at least part of the thickness of the bone 16, even though it is thin. The thread 5 extends forward into the opening of the bone plate 15.

FIG. 6 shows an alternative embodiment of a screw 1 produced with a modified whirling knife without an overcut. The indentation 7 is therefore smaller than in the screw 1 of FIG. 1, although the thread 5 corresponds essentially to the thread 5 of FIG. 1. The first azimuth angle region 9 has no indentation 7. The second azimuth angle range 10, in which the indentation 7 is located, has a value of 45°, for example. The first azimuth angle range 9 then has a value of 315°.

FIG. 7 schematically shows a process step for the manufacture of a screw 1. In this case, a whirling knife (not shown) was used to cut a thread 5 in a rod-shaped ingot material. In the process step shown, the screw 1 is held on the head 4 by means of a contour collet 30 after insertion of the thread 5. In addition, a guide sleeve 33 prevents the screw 1 from tilting when the contour collet 30 is opened. The contour collet 30 has a contour 31 for this purpose, which is designed in such a way that it forms a counter-contour to the head 4 of the screw 1. It is therefore suitable for gripping the head 4 of the screw 1 and holding it securely. However, it would also be conceivable to use other contours that grip, for example, on the head or parts of the head as well as parts of the screw shank or thread. In particular, only a section of the head 4 could also be held. By gripping the screw 1 on the head, as shown here, it is possible to further process the head 4, for example to manufacture a screw drive, here a Torx drive 32. In the present case, the process step is performed with a screw 1 as shown in FIG. 1 or FIG. 6, in which the thread extends into the head. Therefore, gripping by a conventional collet would not be possible, since holding on to the thread 5 would damage the thread 5. The process step shown is therefore particularly suitable for producing a screw according to the invention. However, it is obvious to the person skilled in the art that the process step shown is also suitable for manufacturing a conventional screw.

The invention claimed is:

1. A screw, comprising:
   a shaft with a tip, a head and a thread, as well as a longitudinal axis of the shaft, and a set of radial cross-sectional surfaces of the head passing through the longitudinal axis of the shaft, wherein a position of each of the set of radial cross-sectional surfaces is defined by an azimuth angle in a plane (E) perpendicular to the longitudinal axis, and wherein each of the set of radial cross-sectional surfaces comprises an area defined by the longitudinal axis and an outer surface of the screw, wherein the thread continuously extends from the tip of the shaft to at least the head of the screw, wherein the thread extends into the head in such a way that a surface area of each of the set of radial cross-sectional surfaces in a first azimuth angle range is constant and the surface areas of each of the set of radial cross-sectional surfaces in a second azimuth angle range, which is different from the first azimuth angle range, has a different and smaller value than the surface area of each of the set of radial cross-sectional surfaces in the first azimuth angle range, the first azimuth angle range being at most 350°.

2. The screw according to claim 1, wherein the first and second azimuth angle ranges are each divided into at least two sections distributed at equal azimuth angle intervals.

3. The screw according to claim 2, wherein the first azimuth angle range is at most 330°.

4. The screw according to claim 2, wherein the head has, in the second azimuth angle range, at least one indentation formed by a continuation of the thread.

5. The screw according to claim 4, wherein the head has a number of indentations formed by the continuation of the thread corresponding to the number of sections of the azimuth angle range.

6. The screw according to claim 5, wherein each portion of the azimuth angle range comprises an indentation formed by the continuation of the thread.

7. The screw according to claim 1, wherein the thread is multi-threaded.

8. The screw according to claim 1, wherein the head has, in the second azimuth angle range, at least one indentation formed by a continuation of the thread.

9. The screw according to claim 8, wherein the at least one indentation, which is formed by the continuation of the thread, is arranged on an underside of the head in the region of a thread end.

10. The screw according to claim 1, further comprising geometric centers of each of the set of radial cross-sectional surfaces, wherein a distance between each of the geometric centers of the set of radial cross-sectional surfaces and the longitudinal axis is constant in the first azimuth angle range.

11. The screw according to claim 1, wherein the screw is formed, such that each of the set of radial cross-sectional surfaces is connected.

12. The screw according to claim 1, wherein a first normal cross-section in a plane perpendicular to the longitudinal axis in a head region is at least partially non-circular.

13. The screw according to claim 12, wherein a second normal cross-section is circular and is parallel to the first normal cross-section, and the first normal cross-section is arranged along the longitudinal axis of the screw between the tip of the screw and the second normal cross-section.

* * * * *